United States Patent [19]

Pedroni et al.

[11] Patent Number: 5,622,706

[45] Date of Patent: Apr. 22, 1997

[54] CLONING AND SEQUENCING OF THE GENE WHICH CODES FOR A NEW PILINIC SUBUNIT OF BORDELLA PERTUSSIS

[75] Inventors: Paola Pedroni, Milan; Barbara Riboli, Cremona; Francesca De Ferra, Milan; Guido Grandi, Milan; Salvatore Toma, Milan; Beatrice Aricó; Rino Rappuoli, both of Quercegrossa-Siena, all of Italy

[73] Assignees: Sclavo S.p.A., Siena; Eniricerche S.p.A., Milan, both of Italy

[21] Appl. No.: 334,425

[22] Filed: Nov. 4, 1994

Related U.S. Application Data

[63] Continuation of Ser. No. 177,201, Jan. 3, 1994, abandoned, which is a continuation of Ser. No. 947,375, Sep. 18, 1992, abandoned, which is a continuation of Ser. No. 680,895, Apr. 5, 1991, abandoned, which is a division of Ser. No. 288,169, Dec. 22, 1988, Pat. No. 5,059,537.

[30] Foreign Application Priority Data

Dec. 22, 1987 [IT] Italy ................... 23150-A/87

[51] Int. Cl.⁶ .................. A61K 39/02; A61K 39/10; C07K 14/235; C12N 15/00
[52] U.S. Cl. .................. 424/253.1; 404/184.1; 404/185.1; 404/242.1; 435/69.1; 435/69.3; 435/71.1; 435/253.2; 435/252.33; 435/320.1; 530/350
[58] Field of Search .................. 424/184.1, 69.3, 424/253.1, 242.1, 185.1; 530/350; 435/69.1, 69.3, 71.1, 253.2, 253.33, 320.1

[56] References Cited

PUBLICATIONS

Livey et al Mole. Micro 1987 1(2) 203–209.
Cowell et al Int Imn 1987 55: 916–922.
Mooi et al Microb Pathog 2(6) 1987 473–484 (Abs only).
Mooi et al Microb. Pathogen 2: 473–484, 1987.
Pedroni et al Molecular Microbiology 2:539–543, 1988.
Movi et al Microbiol Pattiogenesis 12:127–135 1992.
Livey et al Mol. Microbiol 1:203–209, 1987.
Cowell et al, Infection & Immunity 55:916–922, 1987.
Livey et al Molecular Microbiology 1(2) 203–209 1987 Cloning & Nucleotide sequence analysis of the serotype 2 fimbriol subunit gene of Bordeletta pertussis.
Cowell et al, Infect & Imm. 55:916–922, 1987 Purification & Characterization of Serotype 6 Fimbriae from Bordeletta pertussis & Comparison of their properties with Serotype 2 fimbriae.
Mooi et al Microb Pathog 2(6) 473–484 1987, Abstract only, Characterization of Frimbral subunits from Bordeletta Species.
GRAS–Masse et al Synthetic Peptides in 'Biology and Medicine, 'pp. 105–112, 1985.
Livey et al Molecular Microbiology 1:203–209 1987.
Cowell et al Infect & Immunity 55:916–922, 1951.
Mooi et al Microb Pathogen. 2:473–484 1987.

Primary Examiner—Hazel F. Sidberry
Attorney, Agent, or Firm—Barbara G. McClung; Robert P. Blackburn; Woodcock Washburn Kurtz Mackiewicz & Norris

[57] ABSTRACT

The cloning and sequencing of the gene which codes for a new pilinic subunit of *Bordetella pertussis* are described. The aminoacid sequence of the mature subunit, deduced from its necleotide sequence, is similar but not identical to that of the known pilins 2, 3 and 6. Polypeptides having the aminoacid sequence of the mature pilinic subunit or of regions thereof are particularly useful for the development of synthetic acellular vaccines against *pertussis*.

1 Claim, 3 Drawing Sheets

```
                                   30                                          60
GAT CCC TTC TTT ACT CCA GCC TGT ATG CAA GCC AAA ACG TTC CTC CTG GGC GCG GCG CTC
Asp Pro Phe Phe Thr Pro Ala Cys Met Gln Ala Lys Thr Phe Leu Leu Gly Ala Ala Leu
                                     ↓ 90                                     120
GCC GGC GTC GCG CTC GCC GCC CAT GCC GAA GAC GGC ACC ATT GTC ATT ACC GGC ACG ATC
Ala Gly Val Ala Leu Ala Ala His Ala Glu Asp Gly Thr Ile Val Ile Thr Gly Thr Ile
                              150                                             180
ACC GAC CAG ACC TGC ACG ATC GAG GAC CCG AGC CCC GGT TAC ATC AAG GTC GTG CAC CTG
Thr Asp Gln Thr Cys Thr Ile Glu Asp Pro Ser Pro Gly Tyr Ile Lys Val Val His Leu
                      210                                                     240
CCC ACG ATC TCC AAG AGC GCG CTG AAG AAC GCC GGC GAC GTG GCG GGG CGC ACT CGC TTC
Pro Thr Ile Ser Lys Ser Ala Leu Lys Asn Ala Gly Asp Val Ala Gly Arg Thr Arg Phe
                              270                                             300
GAT ATC AAG CTG AAG GAC TGC CCG ACC ACC GTC AAC ACT CTC AAG CTG TAC TTC GAG CCC
Asp Ile Lys Leu Lys Asp Cys Pro Thr Thr Val Asn Thr Leu Lys Leu Tyr Phe Glu Pro
                                      330                                     360
GGC CCC ACC ACG GAT TAC GGC ACC AAG GAT CTG AAA GCC TAT AAG CAG GCT TGG TAC GTC
Gly Pro Thr Thr Asp Tyr Gly Thr Lys Asp Leu Lys Ala Tyr Lys Gln Ala Trp Tyr Val
                              390                                             420
GAC GCC GCA ACG CTG CTC AAA TCG CCG CCC AGT GTG ACC GAA GCC AAG GGG GTG CAG ATC
Asp Ala Ala Thr Leu Leu Lys Ser Pro Pro Ser Val Thr Glu Ala Lys Gly Val Gln Ile
                          450                                                 480
CGG CTG ATG AAC CTG AAC GGC AAG CAG ATT CCC ATG GGC GAG ACC GAG CCC AAC CAG CAT
Arg Leu Met Asn Leu Asn Gly Lys Gln Ile Pro Met Gly Glu Thr Glu Pro Asn Gln His
                              510                                             540
GCC GCG GCA TTT TCC GGC ACC ATG CAA GCC GGC CAG GGA CAG AAA TCG TTC ACC TTG CAC
Ala Ala Ala Phe Ser Gly Thr Met Gln Ala Gly Gln Gly Gln Lys Ser Phe Thr Leu His
                              570                                             600
TAC CTG GCC GGC TAC GTG AAG AAG GCC AGT GGA GAG GTC GAG GCG ACC ATG CTG ACC ACC
Tyr Leu Ala Gly Tyr Val Lys Lys Ala Ser Gly Glu Val Glu Ala Thr Met Leu Thr Thr
                              630                                             660
TAC GTG GGC TTT TCG GTC GTC TAC CCC TGA AAC GCA ACC ATG GCG GCC GCG TTG CGC CCT
Tyr Val Gly Phe Ser Val Val Tyr Pro End Asn Ala Thr Met Ala Ala Ala Leu Arg Pro
                              690                                             720
GCG AAC CCC GGC GAT CAG CGC GGC CGC TTG TCG ATG AGC CGC CGC GCC TTG CCC GTC AGG
Ala Asn Pro Gly Asp Gln Arg Gly Arg Leu Ser Met Ser Arg Arg Ala Leu Pro Val Arg
                              750                                             780
GTA CGC TCG ACG AAG CCC GTG TCG GCA ACC TGC ACG CGG GCC TGA CGC CGA TGT ATG ACT
Val Arg Ser Thr Lys Pro Val Ser Ala Thr Cys Thr Arg Ala End Arg Arg Cys Met Thr
                              810                                             840
TGA CCG CAT GCT GCA GCT GCT TGC CCA GGC CGG CGC GCT CGG CCT CGG TCA GGG TGG AGG
End Pro His Ala Ala Ala Ala Cys Pro Gly Arg Arg Ala Arg Pro Arg Ser Gly Trp Arg

ATT C
Ile
```

FIG. 1

| | 1 | 2 | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|---|---|---|---|---|---|---|---|---|---|---|---|
| STX | Glu | Asp | Gly | Thr | Ile | Val | Ile | Thr | Gly | Thr | Ile | Thr | Asp | Gln | Thr | Cys | Thr | Ile | Glu | Asp |
| ST2 | Asp | Asp | Gly | Thr | Ile | Val | Ile | Thr | Gly | Thr | Ile | Thr | Asp | Thr | Thr | Cys | Val | Ile | Glu | Asp |
| ST3 | Asn | Asp | Gly | Thr | Ile | Val | Ile | Thr | Gly | Ser | Ile | Ser | Asp | Gln | Thr | X | Val | Ile | Glu | Asp |
| ST6 | Asn | Asp | Gly | Thr | Ile | Val | Ile | Thr | Gly | Ser | Ile | Ser | Asp | Gln | Thr | X | Val | Ile | Glu | Glu |

FIG. 2

```
1    PheThrProAlaCysMetGlnAlaLysThrPheLeuLeuGlyAlaAlaLeuAlaGlyVal
1    MetGlnIleProPheGlnArgAlaLeuArgLeuCysLeuArgAlaAlaLeuAlaAlaIle

21   AlaLeuAlaAlaHisAlaGluAspGlyThrIleValIleThrGlyThrIleThrAspGln
21   AlaSerAlaAlaHisAlaAspAspGlyThrIleValIleThrGlyThrIleThrAspThr

41   ThrCysThrIleGluAspProSer   ProGlyTyrIleLysValValHisLeuProThr
41   ThrCysValIleGluAspProSerGlyProAsnHisThrLysValValGlnLeuProLys

60   IleSerLysSerAlaLeuLysAsnAlaGlyAspValAlaGlyArgThrArgPheAspIle
61   IleSerLysAsnAlaLeuLysAlaAsnGlyAspGlnAlaGlyArgThrProPheIleIle

80   LysLeuLysAspCysPro   ThrThrValAsnThrLeuLysLeuTyrPheGluProGly
81   LysLeuLysAspCysProSerSerLeuGlyAsnGlyValLysAlaTyrPheGluProGly

99   ProThrThrAspTyrGlyThrLysAspLeuLysAlaTyrLysGlnAlaTrpTyrValAsp
101  ProThrThrAspTyrSerThrGlyAspLeuArgAlaTyrLysMetValTyrAlaThrAsn

119  AlaAlaThrLeuLeuLysSerProProSerValThrGluAlaLysGlyValGlnIleArg
121  ProGlnThrGlnLeuSerAsnIleThrAlaAlaThrGluAlaGlnGlyValGlnValArg

139  LeuMetAsnLeuAsnGlyLysGlnIleProMetGlyGluThrGluProAsnGlnHisAla
141  IleSerAsnLeuAsnAspSerLysIleThrMetGlyAlaAsnGluAlaThrGlnGlnAla

159  AlaAlaPheSerGlyThrMetGlnAlaGlyGlnGlyGlnLysSer   PheThrLeuHis
161  AlaGlyPheAspProGluValGlnThrGly   GlyThrSerSerThrValThrMetArg

178  TyrLeuAlaGlyTyrValLysLysAlaSerGlyGluValGluAlaThrMetLeuThrThr
180  TyrLeuAlaSerTyrValLysLys   AsnGlyAspValGluAlaSerAlaIleThrThr

198  TyrValGlyPheSerValValTyrProEnd
199  TyrValGlyPheSerValValTyrProEnd
```

FIG. 3

CLONING AND SEQUENCING OF THE GENE WHICH CODES FOR A NEW PILINIC SUBUNIT OF BORDELLA PERTUSSIS

This application is a continuation of application Ser. No. 08/177,201, filed Jan. 3, 1994 now abandoned, which is a continuation of application Ser. No. 07/947,375, filed Sep. 18, 1992, now abandoned, which is a Continuation of application Ser. No. 07/680,895 filed Apr. 5, 1991, now abandoned which is a Divisional application of U.S. application Ser. No. 07/288,169, filed Dec. 22, 1988, now U.S. Pat. No. 5,059,537.

The present invention relates to the cloning and sequencing of the gene which codes for a new proteinaceous subunit of the pili of *Bordetella pertussis*.

The invention also concerns a recombinant plasmid which includes the gene or fragments thereof and a host microorganism transformed by the recombinant plasmid.

The present invention also relates to immunologically-active synthetic peptides which have an amino acid sequence identical to that of the proteinaceous subunit or to regions thereof.

Pertussis is a disease of the respiratory tract caused by *Bordetalla pertussis* (*B. pertussis*), a microorganism which is transmitted from a sick person to a susceptible healthy individual during the catarrhal and convulsive stage.

Pertussis may cause convulsions, brain damage and sometimes death, particularly in infants and in newborn babies without maternal anti-pertussis antibodies. An effective vaccine against the disease is therefore particularly desirable.

A cellular vaccine against *pertussis* is currently used which is constituted by virulent bacteria killed with merthiolate and treated at 56° C. and which, whilst providing permanent protection, may induce undesirable side effects. There is therefore a need to develop new accelular vaccines against infection by *B. pertussis* which do not have the disadvantages described above.

An essential step in the pathogenesis of *pertussis* is represented by the adhesion of the bacteria to the epithelial cells of the upper respiratory tract which thus enables the microorganism to elude the defensive system of the host.

Although it is not yet completely clear which components of the cell surface of the bacterium are involved in this process, it seems, however, that this adhesion takes place by means of extracellular proteins constituted by polymerised subunits, known as fimbriae or pili present on the surface of the bacterium.

Ashworth et al. (1982) (Infect. Immun. 37: 1278–1281) first suggested that the fimbriae of *B. pertussis* were serotype-specific agglutinogens, that is superficial antigens which stimulate the production of antibodies which agglutinate the bacterial cells.

Irons and collaborators (Dev. Biol. Standard. 61, 153–163 (1985)) isolated and purified *B. pertussis* fimbriae which were classified as serotype 2 and 3 agglutinogens. The fimbriae appeared to be constituted by subunits with molecular weights of 21,000, 22,000 and 24,000 daltons.

As well as the above agglutinogens, fimbriae of serotypes 1, 4, 5 and 6 have now been isolated and purified. Numerous studies have been carried out concerning their role in adhesion to the epithelial cells (Urisu, T. H. et al (1986) Infect. Immun. 52: 695–701), their immunogenic activtiy (Zhang J. M. et al. Dev. Biol. Stand. 61: 173–185 (1985) and their structure (Zhang J. M. Infect. Immun. 48: 422–427 (1985)), with a view to the use of the fimbriae or subunits thereof for the development of an acellular vaccine which is protective against *pertussis*. Although it has been observed that mice innoculated with purified *B. pertussis* pili were protected against subsequent intranasal infection with the virulent bacterium (Robinson et al (1985) Dev. Biol. Stand. 61: 165–172), the design of an acellular vaccine based on the purified pili or subunits thereof isolated from pili (pilins) must take into account the antigenic variations observed in different strains of *B. pertussis*.

In fact, immunisation with fimbriae of a particular serotype does not always confer protective immunity against infections caused by a strain containing a different serotype.

Thus, for example, anti-serotype 2 antibodies agglutinate only *B. pertussis* cells containing type 2 agglutinogen and the same applies to anti-serotype 6 antibodies (Cowell J. L. et al. (1987) Inf. and Immun. Vol. 55, N.4, 916–922).

Moreover, the observation that anti-serotype 2 and 3 monoclonal antibodies inhibit the binding of *B. pertussis* to VIRO cells in a serotype-specific manner in vitro (Gorringe et al. (1985) FEMS Microbiol. Sect. 26: 5–9) suggests that the fimbriae are antigenically different. It therefore seems to be of fundamental importance to acquire further knowledge concerning the number of different antigenic types of fimbriae which can be expressed by *B. pertussis* in order to be able to develop a completely satisfactory polyvalent acellular vaccine.

The gene which codes for the larger pilinic subunit which corresponds to serotype 2 has recently been cloned and sequenced (Livey J. et al. (1987) Molecular Microbiol. 1 (2) 203–209).

A new gene which codes for a new pilinic subunit of *B. pertussis* has now been isolated and sequenced. The amino terminal sequence of the mature portion of the subunit is similar, but not identical to that of pilins 2, 3 and 6.

A subject of the present invention is therefore the cloning and sequencing of the gene which codes for a new pilinic subunit of *Bordetella pertussis*.

Another subject of the present invention is constituted by a recombinant plasmid, characterised in that it contains the gene which codes for the subunit or fragments thereof, and host microorganisms transformed by the recombinant plasmid.

A further subject of the present invention is constituted by immunologically-active peptides with an amino acid sequence identical to that of the pilinic subunit or to regions thereof.

Another subject of the present invention is constituted by the use of the peptides for the preparation of an acellular vaccine against *pertussis*. Further subjects of the present invention will become clear from a reading of the text and from the examples which follow.

For a better understanding of the present invention, a brief description of the terms used is given below.

Gene Library or genome bank—this term means the set of clones of a host microorganism each of which carries a DNA fragment derived from the donor organism whose bank is to be produced.

A genome bank is defined as representative when the group of individual fragments contained in each clone reconstitute the whole chromosomal DNA of the organism.

Expression—indicates the mechanism by which a host organism can synthesise the protein for which a particular gene codes.

It includes a process of transcription, that is the transmission of the genetic information from the DNA to the messenger RNA (mRNA), and of translation, that is the transmission of the information from the mRNA to the protein according to the rules of the genetic code, described by J. D. Watson (Molecular Biology of the Gene, W. A.

Benjamin Inc. N.Y., 3rd ed. 1976), in which the codons, that is the triplets of nucleotide bases, which code for a particular amino acid are given. Various codons may code for the same amino acid but, for each amino acid, there are only certain codons and no others.

Restriction enzymes—are hydrolytic enzymes which can cut a DNA molecule at specific sites, the recognition sites of the restriction enzymes.

Cloning vectors—are DNA molecules which contain all the genetic information which enable their replication when transferred into a host microorganism. Examples of cloning vectors are plasmids, the DNA of some bacteriophages and cosmids.

Plasmid DNA, which is circular in shape, can be cut by appropriate techniques and a fragment of heterologous DNA can be inserted and the ring reclosed to form a larger molecule:—a recombinant DNA molecule or hybrid plasmid. The vectors are used to insert the heterologous DNA fragments, that is fragments of DNA which code for a protein not generally produced by the organism transformed by the vector.

Primer: is an oligonucleotide of 15–50 bases which is complementary to the region of the single strand which is to be sequenced by an enzymatic method.

BRIEF DESCRIPTION OF THE APPENDED DRAWINGS

FIG. 1 shows the nucleotide sequence of the gene which codes for STX pilin obtained from the SA1 strain of *B. pertussis* and the corresponding amino acid sequence.

The synthetic oligonucleotides used for identifying and sequencing the gene are indicated by the arrows (→ ←).

The initial methionine, the first amino acid of the mature protein and its stop codond are shown.

The cutting site between the mature portion of STX pilin and the signal sequence is indicated by the arrow (↓). The Bam HI and Eco RI restriction sites are underlined (------).

FIG. 2 shows the comparison between the $NH_2$ terminal sequences of the mature portions of the STX, ST2, ST3 and ST6 pilins.

The identical amino acid residues are grouped in boxes.

FIG. 3 homology between STX pilin (top row) and ST2 pilin (bottom row).

Recent progress in the cloning of genes associated with the virulence of *B. pertussis* indicates that the most suitable methods for their identification are those which are based, not on the direct expression of the genes in *E. coli* (Locht et al. (1986) Nucleic Acid Res. 14: 3251–3261; Nicosia et al (1986) P.N.A.S. USA 83: 4631–4635), but on the identification, with the use of specific probes, of the cloned DNA fragments which contain the genes.

According to the present invention, therefore, the amino terminal region of the principal proteinaceous subunit of the fimbriae of *B. pertussis* strain 165 (serotype 1, 2, 3) has been sequenced by means of Edmans degradation and purified by the method described by Zhang, J. M. et al (1985); Dev. Biol. Stand. 61: 173–185).

The amino acid sequence shown below:

```
      1     2    3    4   5   6   7   8   9  10  11  12
NH—Asp—Asp Gly—Thr Ile Val Ile Thr Gly Thr Ile Thr
``` which was subsequently confirmed as being identical to that of the major subunit of the fimbriae of serotype 2 (Livey J et al. Molecular Microbiol. (1987) 1 (2) 203–209), was used to synthesise oligonucleotides, account being taken of the relative degeneracy of the genetic code.

The region which corresponds to amino acids 7–12 was selected for this purpose and a family of oligonucleotides, representative of all the possible combinations of triplets, with the third base degenerate was synthesised by means of an automatic system.

This family was designated probe A, and is shown below:

| | | | | | |
|---|---|---|---|---|---|
| 7 | 8 | 9 | 10 | 11 | 12 |
| Ile | Thr | Gly | Thr | Ile | Thr |
| ATC | ACC | GGC | ACC | ATC | AC |
| T | T | T | T | T | |
| A | G | G | G | A | |
| | | A | | | |

The probe A, marked by the method of Arrand J. E. (Nucleic Acid Hybridisation: A Practical Approach, Edited by B. D. Hames—S. Higgins, Press Washington D.C. 1985, P. 34) was then used to identify within a *B. pertussis* gene library those clones which carry the chromosomal DNA fragment which hybridises with the probe.

According to the present invention, a gene library representative of the genome of *B. pertussis*, was constructed by the digestion of the chromosomal DNA of the bacterium with suitable restriction enzymes.

Various strains of *B. pertussis* may be used for this purpose.

In particular the commercially available *B. pertussis* strain 165 (serotype 1, 2, 3) (SCLAVO) was used.

The chromosomal DNA of this strain was extracted from the lysed cells, digested with Sau3A restriction enzyme in the manner suggested by the suppliers and recovered by precipitation with ethanol and centrifuging. The chromosomal DNA fragments thus obtained were then introduced into a cloning vector and, after hybridisation with the probe A, were sequenced by the method of Sanger F. et al (1977) (P.N.A.S. 74, 5463).

This method is based on an enzymatic sequencing system and is particularly suitable for the determination of sequences of long and little-known DNA fragments.

It requires the availability of the fragment which is to be sequenced in single stranded form, and of a small primer oligonucleotide (15–50 bases) which is complementary to the initial region of the single strand. The DNA fragments were accordingly cloned in an M13 phage vector. The preferred phage vectors used were M13mp8 (Messing J. et al. (1981) Nucleic Acid Reser. 9, 309) and M13mp9 (Messing J. et al. (1982), Gene, 19 263) in which the position of the cloning sites is arranged in a reverse manner to the annealing site of the primer enabling the sequence of an insert to be defined starting from the two opposite ends. In practice, the phages, digested beforehand with BamHI enzyme, were ligated to the DNA fragments in the presence of T4 DNA ligase enzyme by generally known techniques.

The ligation mixture was then used to transform *E. coli* cells made competent with $CaCl_2$ by the technique described by Mandel M. and Higa (1970) (J. Mol. Biol. 53, 154).

The transformants were then selected on a suitable culture medium at a temperature of from 35° to 40° C. over night.

The positive plaques (white) thus obtained were then transferred to nitrocellulose filters and hybridised with the probe A marked according to J. E. Arrand's method.

Of the plaques which gave a positive hybridisation signal, two were then used for the sequencing of the single stranded DNA by Sanger's method, with the use of the successive primers strategy (Strauss E. C. et al. 1986, Anal. Biochem. 154, 353).

It was thus found that the sequence of the single strand of one plaque contained a nucleotide region which is identical to that deduced from the N-terminal amino acid sequence used for the preparation of the probe and corresponds to the N-terminal region of the serotype 2 pilinic subunit for which the ST2 gene codes.

The single strand of the other plaque however contained a region with a nucleotide sequence which is similar but not identical to that of the ST2 gene, which suggested the presence of a different gene.

Since this clone contained only a portion of the gene, designated STX, in order to obtain the whole chromosomal DNA fragment containing the gene, a gene library of B. pertussis was constructed with the use of a cosmid as the cloning vector.

Cosmids are certain plasmids in which the cos end of the lambda phage has been inserted. They enable the recombinant molecule to be packed with the viral proteins so as to form viral particles. The DNA of the cosmids is then injected into the bacteria by the viral particle as if it were lambda DNA.

Since lambda DNA is very large whilst the cosmid is relatively small, long fragments of DNA can be inserted in the vectors.

In practice the cosmid pCH79 (Hohn B. et al. (1980) Gene 11: 291–298) and the B. pertussis strain SA1 (Arico, B. and Rappuoli R. (1987) J. Bacteriol. 169: 2847–2853), were used.

The chromosomal DNA of B. pertussis SA1 was separated from the lysed cells and partially digested with SAu3A enzyme.

After precipitation by ethanol and separation by centrifuging, the chromosomal DNA fragments of 35–45 kbases were isolated and ligated in the presence of T4DNA ligase, with the cosmid which had previously been digested with Bam HI enzyme. This ligation mixture was then used to transform E. coli cells and the transformants were selected on a selective medium to which ampicillin had been added.

The positive colonies were then analysed by the hybridisation technique with the use of two pairs of probes: 1–2 and 3–4, which are complementary to different portions of the previously-determined region of STX and ST2.

In particular, the probes, which are synthesised by means of an automatic system, have the following sequences:

| | |
|---|---|
| Probe 1 (STX) | C C G C C C A T G C C G A A G A C |
| Probe 2 (STX) | G C C G G T A A T G A C A A T G G |
| Probe 3 (ST2) | C C T T C A G C T T G A T G A T |
| Probe 4 (ST2) | G T G A T G A C G A T G G T G |

The colonies were transferred to nitrocellulose filters, lysed and then hybridised in parallel with the two pairs of probes.

The prehybridisation process was carried out for the two pairs of probes at 65° C. for 6 hours, whilst the hybridisation process was effected at different temperatures for each of the four probes. Some positive clones were thus identified which hybridised with both the probes of a pair.

In order to identify the cosmid and/or cosmids containing the chromosomal DNA fragment including the STX gene, the cosmids were extracted from the positive clones by the rapid extraction method (Maniatis et al. (1982) "Molecular Cloning: A Laboratory Manual", Cold Spring Harbor N.Y.) and analysed by digestion with Eco RI.

It was thus found that one of them, indicated below as pSM 280, contained a sequence identical to the previously identified portion of the STX gene. According to the present invention and in order to sequence the gene, a fragment of the chromosomal DNA of B. pertussis SA1 which hybridises with the specific probe for STX, was extracted from the cosmid pSM 280 and subcloned in a vector of E. coli.

Vectors suitable for the purposes of the present invention may be selected from plasmids, viruses, and bacteriophages generally used in recombinant DNA techniques.

In particular, the plasmid pUC12 (2730 bp) described by Messing J. et al. (1982) (Gene, 19, 259) which enables the quick and easy identification of the clones which have incorporated an extraneous DNA fragment, was used.

In fact the plasmid is a carrier of the genes for β-lactamase and for β-galactoxidase and thus enables the E. coli strain which hosts it to grow on a medium containing ampicillin. When an extraneous fragment is inserted between the restriction sites present in the gene for β-galactoxidase, which are particularly suitable for cloning, the gene is interrupted and is no longer able to produce the enzyme.

It is thus possible, with the use of substances similar to galactose, which can produce molecules which are chromogenic even if degraded, to distinguish the recombinant clones (not coloured) from those containing the plasmid.

According to the present invention, the pSM 280 cosmid was digested with Eco RI restriction enzyme and the digestion mixture was loaded in duplicate on to agarose gel.

After electrophoresis, the DNA bands were transferred to nitrocellulose filters and hybridised with the probes 1 and 2, suitably marked.

The pre-hybridisation treatment and the hybridisation treatment were carried out under different operative conditions for each probe. The filters were then washed appropriately and subjected to radiography.

The results obtained showed a single positive band of 1.2 Kilobases (Kb) for both probes.

The chromosomal DNA fragment corresponding to the band was electroeluted and ligated to the plasmid pUC 12 which had previously been digested with Eco RI.

The ligation reaction was carried out in a buffer mixture in the presence of T4 DNA ligase with the use of a plasmid/DNA fragment ratio in the favour of the fragment, preferably 1:3.

Upon completion of the ligation reaction, the mixture was used to transform competent E. coli cells and the transformants were selected on a culture medium to which ampicillin had been added.

From the positive clones thus obtained, some which contained the required recombinant plasmids were isolated.

One of these, designated pSM 281, was used to isolate and sequence the 1.2 kb chromosomal DNA fragment.

The sequencing was carried out by Sanger's method with the use of the successive primers strategy.

The sequencing reactions were carried out on the denatured plasmids according to the normal Boehringer protocol with the use of a "pUC Sequencing" kit and with the use of ATP as the α $[P^{32}]$ tracer.

By means of the operation described above, it was found that the 1.2 Kb fragment is constituted by a 375-base region of the cosmid pHC79 and by a 844-base region of the STX gene, whose nucleotide and amino acid sequences are given in FIG. 1.

An open reading frame was identified in the sequence which extends from the 5' terminal of the 844-base region to the stop codon situated 628 bases downstream. Moreover, the nucleotide and the amino acid sequences of the mature protein for which the STX gene codes were identified, on the basis of the similarity with the amino terminal sequence of the ST2 subunit.

This sequence, represented by the N-terminal amino acids NH-Glu-Asp-Gly-Thr-Ile-Val-Ile-Thr-Gly, is preceded by the Ala-Ala-His-Ala tetrapeptide which is identical to that present between the mature protein of the pilinic subunit ST2 and its secretion signal (leader sequence). The tetrapeptide, which represents the specific cutting site for a membrane leader-peptidase, is preceded by an amino acid sequence of 29 amino acids which contains a central hydrophobic domain (amino acids −6 to −16), which is characteristic of leader sequences, and a methionine in position −21.

The ATG which codes for the Met in position −21 is, very probably, the translation codon. In fact the sequence downstream of the codon up to the start of the mature protein (GAA), codes for a polypeptide which has the length and characteristics typical of a signal sequence (Periman, D. et al. (1983), J. Mol. Biol. 167, 391–409).

The amino acid sequence of the STX gene product, deduced from its nucleotide sequence, shows a considerable similarity to the ST2 gene product. A great similarity between the two proteins was observed in the amino terminal region and in the carboxy terminal region of 12 amino acids which, as shown for other pilinic proteins, are those which have the highest degree of conservation (Livey at al (1987) Molecular Microbiol., 1 (2), 203–209).

The overall degree of similarity of the mature proteins is estimated as 66% at the amino acid level and 61% at the nucleotide level.

The presumed signal sequence of STX has a slightly lower similarity (52%) to that of the subunit ST2 than the rest of the protein. Moreover, the hydrophobicity/hydrophilicity model predicted by the sequences of ST2 and STX is very similar.

In conclusion, the STX gene of *B. pertussis* codes for a pilin-type mature protein with a molecular weight of approximately 20 kd, which could correspond to a serotypically-different pilin 2, 3 or 6 or to a new pilin.

According to the present invention and in order to identify the relationships existing in the chromosomal DNA of *B. pertussis* between the two genes ST2 and STX, a genome analysis was carried out.

In particular, the chromosomal DNA of *B. pertussis* 165 was digested with various restriction enzymes and the digestion mixtures were hybridised with probes specific for the STX and ST2 genes.

In no case was a band identified which could hybridise with both probes.

This idicated that these two genes were not situated in a single operon, or near each other, but that they must be situated at a minimum distance of several kilobases.

This observation was also confirmed by the absence of a cosmid containing both the genes from the gene library of *B. pertussis* SA1.

According to the present invention, peptides with an amino acid sequence identical to that of the mature protein for which the STX gene codes, or to immunologically-active regions thereof, are particularly useful for the preparation of acellular polyvalent vaccines against *pertussis*. The plasmid pSM 281 was deposited on Jul. 12, 1987 as *E. coli* JM 103 (pSM 281) at the American Type Culture Collection, 12301 Parklawn Drive, Rockville, Md. 20852, as ATCC 67572.

The following experimental examples are illustrative of the invention and not limiting.

EXAMPLE 1

Extraction of the Chromosomal DNA from *B. pertussis* 165

100 ml of fermentation medium having the following composition:

| | |
|---|---|
| Beta casamino acids (DIFCO) | 14 g |
| KCl | 0.2 g |
| MgCl$_2$.6H$_2$O | 0.1 g |
| K$_2$PO$_4$ | 0.5 g |
| nicotinic acid | 0.02 g |
| glutathione | 0.01 g |
| starch | 1.00 g |
| H$_2$O | 1 l |
| pH 6.8 | | previously sterilised at 120° C. for 15 minutes, was innoculated with *B. pertussis* strain 165 (serotype 1, 2, 3) and kept under agitation (200 revolutions per minute, r.p.m.) at 37° C. for 3 days.

At the end of this period, the cells were separated from the supernatant liquid by centrifuging (10 minutes, 5000 rpm) in a Sorvall RC5B model SS34 rotor at 4° C. and washed (2×120 ml) with a solution containing 100 mM NaCl, 50 mM Tris-HCl pH 7.5.

The suspension thus obtained was centrifuged again as described above and the cells were recovered and resuspended in 10 ml of a buffer solution (100 mM EDTA, 50 mM NaCl, 2.5% sucrose, pH 6.9) containing 1 mg/ml of lysozyme (SIGMA). The suspension was agitated and kept at 37° C. for 30 minutes and SDS (sodium dodecyl sulphate) was then added up to a final concentration of 1% and kept at 60° C. for 30 minutes.

1 mg/ml of proteinase K, previously incubated at 37° C. for 30 minutes in 1×SSC (1×SSC=0.15M NaCl, 15 mM sodium citrate), was then added to the solution and the resulting mixture was reacted at 37° C. for 2 hours. After the addition of NaCl to a final concentration of 1M, the mixture was kept in ice for 30 minutes and then centrifuged. The DNA contained in the supernatant liquid was precipitated with 2–3 volumes of cold ethanol (−20° C.), collected with a glass rod and resuspended in 10 ml of 0.1×SSC. The suspension was kept at ambient temperature (20°–25° C.) with gentle agitation for one night and, after the addition of RNAse (10 γ/ml), at 37° C. for 30 minutes.

The saline concentration of the solution was then brought to 1×SSC, extracted with phenol (1 volume), and the DNA precipitated by the addition of isopropanol dropwise to the solution which was kept at ambient temperature with gentle agitation.

The DNA was then recovered by centrifuging and resuspended in 1 ml of 0.1×SSC.

The quantity of chromosomal DNA, evaluated by spectrophotometric reading at OD260 with the use of a Perkin-Elmer spectrophotometer mod. 515, was 0.645 mg/ml.

EXAMPLE 2

Isolation and Sequencing of the Gene which Codes for a Pilinic Subunit.

A) Preparation of the Gene Library of *B. pertussis* 165 in Sau3A.

10 μg of chromosomal DNA obtained as described in Example 1 were digested in 200 μl of a reaction buffer (6 mM Tris-HCl pH 7.5, 50 mM NaCl, 5 mM MgCl$_2$) with 100 units (U) of Sau3A restriction enzyme (Boheringer) at 37° C. for 1.5 hours.

The DNA thus digested was precipitated by the addition of 3M sodium acetate and ethanol to the mixture, separated by centrifuging at 4° C. for 15 minutes at 12,000 rpm in an Eppendorf centrifuge and then resuspended in 100 µl of TE buffer (10 mM Tris-HCl pH 8.0, 1 mM EDTA). Simultaneously, the phages M13mp8 (5 ug) and M13mp9 (5 µg) were digested separately with 20 U of Bam HI (Boheringer) enzyme in 50 µl of reaction buffer (10 mM Tris-HCl pH 7,8, 10 mM MgCl$_2$, 50 mM NaCl) at 37° C. for 1.5 hours.

The phage DNA was then precipitated from the digestion mixture, separated by centrifuging and resuspended in TE buffer as given above.

15 µl of the solution containing the chromosomal DNA fragments (1.5 µg) were then ligated with 12.5 µl of the phage DNA solution (1.25 ug) in 1.25 ml of ligation buffer (66mM Tris-HCl pH 7.6, 1 mM ATP, 10 mM MgCl$_2$, 10 mM dithiothreitol) in the presence of 1 U of T4 DNA ligase at 14° C. for 18 hours.

125 µl portions of the ligation mixture were then used to transform *E. coli* 71/18 cells (Miller, J. H. (1972) Experiments in Molecular Genetics, Cold Spring Harbor Lab. New York) made competent by treatment with 50 mM CaCl$_2$ (Mandel M and Higa (1970) J. Mol. Biol. 53, 154). The selection of the transformants was then carried out by the placing of the cells on 1×YT medium plates (8 g/l Bacto Triptone (DIFCO), 5 g/l Bacto-yeast extract (DIFCO) and 5 g/l NaCl) made selective by the addition of 50 µg/ml of ampicillin, 0.03 mM IPTG (isopropyl-β-D-thiogalactopyranoside), 0.05% X-Gal (5-bromo-4-chloro-3-indolyl-D-galactopyranoside) and incubated for 12 hours at 37° C. in a thermostatically-controlled chamber.

14,000 positive plaques (white) were thus obtained.

B) Construction of the Specific Probe

The N-terminal portion of the larger proteinaceous subunit (2) of the pili of *B. pertussis* 165 was analysed by Edman degradation and had the following sequence:

```
       1   2   3   4   5   6   7   8   9  10  11  12
NH—Asp—Asp Gly—Thr Ile Val Ile Thr Gly Thr Ile Thr
```

The nucleotide sequence deduced from the amino acid sequence was then used to synthesise oligonucleotides for use as probes, account being taken of the relative degeneracy of the genetic code. In particular, a System 1 Plus DNA synthesiser (Beckman) automatic system was used to synthesise a family of oligonucleotides with the following sequence:

| 7   | 8   | 9   | 10  | 11  | 12  |
|-----|-----|-----|-----|-----|-----|
| Ile | Thr | Gly | Thr | Ile | Thr |
| ATC | ACC | GGC | ACC | ATC | AC  |
| T   | T   | T   | T   | T   |     |
| A   | G   | G   | G   | A   |     |
|     |     | A   |     |     |     |

0.9 µg of the oligonucleotides were marked at the 5' OH end with 500 µCi of γ(P$^{32}$) ATP (3000 Ci/mmole) according to the method of Arrand J. E. (Nucleic Acid Hybridisation: A Practical Approach, edited by B. D. Hames—S. Higging, Press Washington D.C. 1985, p 34). The calculated specific activity (LS 7500 Beckman scintillator) was 8.3×10$^8$ cpm/µg of DNA.

C) Screening by Means of the Specific Probe

The plaques of the gene library in M13 were transferred to nitrocellulose filters (Schleicher & Schnell 0.45 µm) and the filters were then hybridised with the specific probe by the method of P. J. Mason and J. Williams (Nucleic Acid Hybridisation: A practical Approach p. 123). The prehybridisation treatment was carried out at 39° C. for 6 hours whilst the hybridisation was carried out at 39° C. for 18 hours. Finally the filters were washed at 25° C. with 0.1% sodium docecyl sulphate (SDS), 6×SSC (O.P.M NaCl, 0.09M Na citrate) for 1 hour and put in contact with Kodak X-Omat AR radiographic plates.

5 plaques which gave the positive signal were thus identified. Two of these were then characterised.

D) Sequencing of the Single Strands Obtained from the Positive Plaques.

The single strands of the two positive plaques were extracted by the technique of Messing J. (1983) (Methods of Enzymol, V.101) and sequenced by means of the successive primers strategy described by Strauss E. C. et al. (1986) (Analytical Biochem. 154, 353). The sequence of one of the single strand contained a region identical to that of the ST2 gene whilst the other contained a similar, but not identical sequence which suggested the presence of a different gene, hereinafter termed STX.

EXAMPLE 3

Sequencing of the Gene STX

A. Construction of a Genome Bank of *B. pertussis* SA1

In order to obtain the entire coding sequence of the gene designated STX, a genome bank of *B. pertussis* SA1 was constructed with the use of the cosmid pHC79.

500 µg of the chromosomal DNA of *B. pertussis* SA1 extracted as described in Example 1 were partially digested with 5 U of Sau 3A restriction enzyme at 37° C. for 15 minutes.

The DNA thus digested was precipitated by the addition of ethanol to the solution and, after separation, was resuspended in 0.5 ml of 10 mM Tris, 1 mM EDTA buffer.

The solution was loaded on to a sucrose gradient of from 10% to 40% dissolved in 35 ml of 1 mM NaCl, 10 mM Tris, 1 mM EDTA buffer (pH 7.5).

The gradient was then centrifuged at 26,000 rpm for 16 hours in a Beckman SW 28 rotor.

Fractions, each of 1 ml, were then collected and the molecular weight of the DNA contained in each fraction was determined by electrophoresis on agarose (Maniatis T. et al. "Molecular Cloning A Laboratory Manual". Cold Spring Harbor N.Y. (1982)).

The fractions containing DNA fragments of 35–45 kb were then dialysed and the DNA precipitated with ethanol as described above.

The DNA was then separated by centrifuging and resuspended in a 10 mM Tris, 1 mM EDTA buffer (pH 7.5) at a concentration of 1 μg/μl of DNA.

The chromosomal DNA fragments were then cloned.

20 μg of the cosmid pHC79 were digested with 40 U of Bam HI enzyme at 37° C. for 1 hour in 200 μl of digestion mixture.

2 μg of chromosomal DNA were then ligated with 0.5 ug of the DNA of the cosmid in 10 μl of ligation mixture in the presence of 1 U of T4 DNA ligase at 14° C. for 18 hours.

At the end of this period, 2.5 μl of the ligation mixture were used in vitro with a Stratagene Packagene Kit.

The recombinant cosmids thus obtained were used to infect the JM109 strain of E. coli and the transformants were selected on LB medium (Bacto Triptone 10 g, Bacto Y. E. 5 g, NaCl 10 g, H$_2$O 1 l, pH 7.5).

Approximately 15,000 positive colonies were produced.

1500 of the colonies were then screened with two pairs of probes have the following sequences:

| | |
|---|---|
| Probe 1 (STX) | C C G C C C A T G C C G A A G A C |
| Probe 2 (STX) | G C C G G T A A T G A C A A T G G |
| Probe 3 (ST2) | C C T T C A G C T T G A T G A T |
| Probe 4 (ST2) | G T G A T G A C G A T G G T G |

The oligonucleotides were synthesised by the Beckman automatic system and marked at the 5' OH end with 105 µCi of γ (P$^{32}$)ATP by the following method.

200 ng of oligonucleotides were suspended in 30 µl of an aqueous solution constituted by 3 µl of Kinase buffer (Boehringer), 21 µl ATP, T4 polynucleotide kinase 10 UX µl (1 µl).

The mixture was kept at 37° C. for 45 minutes and the enzyme deactivated at 65° C. for 10 minutes.

The marked probes were then purified in a Sephadex G-50 column in pH8 TE buffer to eliminate the marker which had not been incorporated.

13 fractions of 150 µl each were collected.

2 µl of each fraction were put in 4 ml of scintillating liquid and measured in the scintillator.

The colonies of the bank, in cosmids, were transferred to nitrocellulose filters (Schleicher and Schuell 0.45 µm) and after lysis with NaOH, their DNA was immobilised by Southern's technique (Maniatis 1982); The filters were hybridised in parallel with the two pairs of probes marked as described above.

The prehybridisation treatment was carried out at 65° C. for 6 hours whilst the hybridisation was carried out at:
53° C. for probe 1
47° C. for probe 2
41° C. for probe 3
45° C. for probe 4
for 18 hours.

The filters were then washed and put in contact with radiographic plates as described in point C) of Example 2.

5 clones which hybridised with the four probes were isolated by the method described above.

The cosmids extracted from the clones were analysed by digestion with Eco RI and it was found that: three of them contained sequences similar but not identical to probes 3 and 4, one contained a sequence identical to the previously-isolated region of the STX gene and the last, which hybridised with probes 1 and 3, contained a sequence which was not identical to that of the STX gene.

The clone containing the cosmid with the STX gene was designated pSM 280.

B) Subcloning of the DNA Fragment Containing the STX Gene

The cosmid pSM280 was extracted by rapid extraction and 250 ng were then digested in 10 µl of 100 mM Tris-HCl pH 7.5, 50 mM NaCl, 10 mM MgCl$_2$ digestion mixture with 5 U of Eco RI (Boheringer) at 37° C. for 1 hour.

The enzymatic reaction was then stopped at 65° C. for 10 minutes and the mixture was loaded in parallel on to two 0.8% agarose gels and, after electrophoresis at 80 volts for 3 hours, the bands of DNA were transferred to 2 nitrocellulose filters (Micro Filtration System 0.45 µm) and then hybridised with the probes 1 and 2 by the technique described in point C).

The prehybridisation treatment was carried out in 10 ml of 6×SSC (1×SSC=150 mM NaCl, 25 mM Na citrate), 10×Denhardt's (1×Denhardt's=1% Ficoll, 1% PVP, 1% BSA Pentax fraction V) and 50 µg/ml of denatured salmon sperm, at 53° C. for 4 hours for filter No. 1 and at 47° C. for 4 hours for filter No. 2.

The hybridisation was carried out in 10 ml of the mixture described above with the addition of 600 µl of probe 1 (6×10$^8$ cpm/γ DNA) for the filter No. 1 and 600 µl of probe 2 (8.4×10$^8$ cpm/γ DNA) for filter No. 2.

The filters 1 and 2 were then incubated at 53° C. and 47° C. respectively for one night. Finally the filters were washed four times for 15 minutes each with 100 ml of 6×SSC containing 0.1% of sodium dodecyl sulphate (SDS) and placed in contact with Kodak X-Omat AR radiographic plates at −80° C. for 1 night.

The results showed a single positive band of 1.2 kbases with both probes.

B) Subcloning of the 1.2 kbase Eco RI Fragment in PUC12.

1 µg of the vector pUC12 was digested in 10 µl of digestion mixture with 5 U of Eco RI at 37° C. for 1 hour.

The enzymatic reaction was deactivated at 65° C. for 10 minutes and the DNA precipitated with ethanol and separated by centrifuging.

50 ng of the digested plasmid DNA were then ligated with 66 ng of the 1.2 kbase Eco RI fragment of DNA in 25 µl of ligation mixture in the presence of 1 U of T4 DNA ligase at 12° C. for 1 night.

20 µl of the ligation mixture were used to transform 200 µl of competent E. coli JM 103 cells (Maniatis, 1982). The selection of the transformants was then carried out on LB agar medium plates with the addition of 50 γ/ml of ampicillin, 40 γ/ml X gel and 125 γ/ml of IPTG at 37° C. for 18 hours.

24 positive clones were obtained, of which 17 contained the required recombinant plasmids.

One of these plasmids, designated pSM 281, was then extracted from the positive clones by means of rapid extraction.

C) Sequencing of pSM 281

The recombinant plasmid pSM281 was sequenced by the method of Sanger et al. (1977) (P.N.A.S. 74, 5463) by means of the successive primers strategy described by Strauss et al (Anal. Biochem. 154, 553 (1986). The oligonucleotides used as primers were synthesised by means of an automatic 1 Plus DNA Synthesiser system (Beckman).

The sequencing reactions were carried out according to the normal Boehringer protocol on the denatured plasmids with the use of a "pUC Sequencing" kit, and with α [P$^{32}$] dATP as the tracer.

The apparatus used for the electrophoretic separation was a Macrophor sequencing System (LKB).

The entire 1.2 kbase fragment thus sequenced consisted of 375 bases of the cosmid pHC79 and 844 bases of the STX gene (FIG. 1).

As shown in FIG. 3, the amino acid sequence of the STX gene product has a considerable similarity to the product of the ST2 gene.

Genome Analysis

The chromosomal DNA of B. pertussis 165 was extracted as described in Example 1 and the portions of the DNA were digested separately with various enzymes.

In practice, 1.5 ug of chromosomal DNA were treated with 15 U of each of the following enzymes Stu I, Sph I, Sma I, Pvu II, Pst I, Eco RI and Bam HI at 37° C. for 3 hours in 20 ml. of digestion mixture.

The mixtures were then loaded onto 0.8% agarose gel and run at 100 V for 3–4 hours.

The bands of chromosomal DNA were then transferred to nitrocellulose filters and hybridised separately with the probes 1 and 4 as described in Example 2.

In no case was a single band identified which was capable of hybridising the two probes.

This indicates that these two genes are not situated in a single operon or near each other, but that they must be at a minimum distance of several kbases.

This observation is confirmed by the absence from the gene library of *B. pertussis* of a cosmid which contains both the genes.

We claim:

1. An immunologically-active synthetic peptide comprising the amino acid sequence of mature STX depicted in FIGS. 1(*a*)–(*b*).

* * * * *